US00PP28566P2

(12) United States Plant Patent
Clark et al.

(10) Patent No.: US PP28,566 P2
(45) Date of Patent: Oct. 24, 2017

(54) COLEUS PLANT NAMED 'UF13-42-4'

(50) Latin Name: *Solenostemon scutellarioides*
Varietal Denomination: UF13-42-4

(71) Applicant: Florida Foundation Seed Producers, Inc., Marianna, FL (US)

(72) Inventors: David G. Clark, Gainesville, FL (US); Grayson M. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/999,961

(22) Filed: Jul. 19, 2016

(51) Int. Cl.
*A01H 5/00* (2006.01)

(52) U.S. Cl.
USPC ..... Plt./373

(58) Field of Classification Search
USPC ..... Plt./373, 469
CPC ..... A01H 5/00
See application file for complete search history.

(56) References Cited

U.S. PATENT DOCUMENTS

PP25,626 P3 6/2015 Clark et al.
PP25,627 P3 6/2015 Clark et al.
PP25,650 P3 6/2015 Clark et al.
PP25,651 P3 6/2015 Clark et al.
PP25,652 P3 6/2015 Clark et al.
PP25,653 P3 6/2015 Clark et al.
2015/0359154 P1 12/2015 Clark et al.
2015/0359155 P1 12/2015 Clark et al.
2015/0359156 P1 12/2015 Clark et al.
2015/0359157 P1 12/2015 Clark et al.
2015/0359158 P1 12/2015 Clark et al.
2016/0212903 P1 7/2016 Clark et al.
2016/0212904 P1 7/2016 Clark et al.

OTHER PUBLICATIONS

U.S. Appl. No. 14/999,963, filed Jul. 19, 2016, Clark et al.
U.S. Appl. No. 14/999,962, filed Jul. 19, 2016, Clark et al.
U.S. Appl. No. 14/545,807, filed Jun. 22, 2015, Clark et al.
U.S. Appl. No. 14/545,808, filed Jun. 22, 2015, Clark et al.
U.S. Appl. No. 13/986,163, filed Apr. 5, 2013, Clark et al.
Nguyen et al., "Genetics of growth habit and development of new coleus (*Solenostemon scutellarioides* (L.) Codd) varieties with trailing habit and bright color," *J Heredity* 99:573-580, 2008.

*Primary Examiner* — Kent L Bell
(74) *Attorney, Agent, or Firm* — Dentons US LLP

(57) ABSTRACT

'UF13-42-4' is a new coleus plant distinguished by having consistent deep red leaves, vigorous but compact growth habit, and desirable non-flowering characteristics, as disclosed herein.

3 Drawing Sheets

Latin name of the genus and species of the plant claimed: *Solenostemon scutellarioides*.

Cultivar denomination: 'UF13-42-4'.

BACKGROUND OF THE INVENTION

The invention relates to a new and distinct cultivar of coleus plant named 'UF13-42-4'. 'UF13-42-4' originated from an open pollination conducted in May-November 2011 in Gainesville, Fla. between the female coleus plant 'UF12-58-2' (unpatented) and an unknown male coleus plant. A single seedling was chosen in May 2013 for further asexual propagation in Gainesville, Fla.

'UF13-42-4' has been reproduced asexually for over two years through vegetative cuttings and has been found to retain its distinctive characteristics through successive asexual propagations. 'UF13-42-4' was first propagated asexually by meristem tip cuttings in May 2013 in Gainesville, Fla., and has remained true-to-type since that time.

'UF13-42-4' has not been made publicly available more than one year prior to the filing date of this application.

When compared to the female parent 'UF12-58-2', 'UF13-42-4' has large, deep red colored leaves and a compact branched habit, while 'UF12-58-2' has slightly smaller leaves colored deep red with distinct golden yellow margins and a less vigorous and more upright plant habit.

When 'UF13-42-4' is compared to the commercial cultivar 'UF06-40-1' (unpatented; trade name Big Red Judy®), both plants have large deep red colored leaves and stems, but 'UF13-42-4' is more brightly colored in both sun and shade conditions. Both plants have a vigorous growth habit, but 'UF13-42-4' is more highly branched and compact, resulting in more densely packed foliage than 'UF06-40-1'. 'UF13-42-4' has not been observed to flower, whereas 'UF06-40-1' flowers profusely.

SUMMARY OF THE INVENTION

The following are the most outstanding and distinguishing characteristics of 'UF13-42-4' when grown under normal horticultural practices in Gainesville, Fla. 'UF13-42-4' has a combination of a novel, vigorous, compact, upright growth habit, excellent heat tolerance, and consistent deep red colored leaves. 'UF13-42-4' has superior stability in foliage color in both sun and shade conditions, maintaining stable color in all conditions. 'UF13-42-4' has a vigorous but compact upright growth habit with excellent lateral branching when grown as a stock plant, thus providing ample vegetative propagules for producers. Due to the plant never being observed to produce flowers in Gainesville, Fla., 'UF13-42-4' is desirable for long-season performance in the landscape.

BRIEF DESCRIPTION OF THE DRAWINGS

This new coleus plant is illustrated by the accompanying photographs, which show the plant's form and foliage.

The colors shown are as true as can be reasonably obtained by conventional photographic procedures.

FIG. 2—shows the growth habit, form, and foliage of the claimed plant.

FIG. 3—shows a close-up of the foliage.

DETAILED BOTANICAL DESCRIPTION

Figure 1:
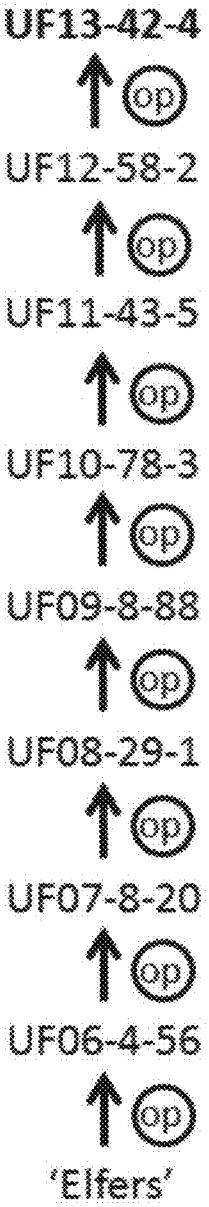
FIG. 1—shows the pedigree of the claimed plant.
Figure 2:
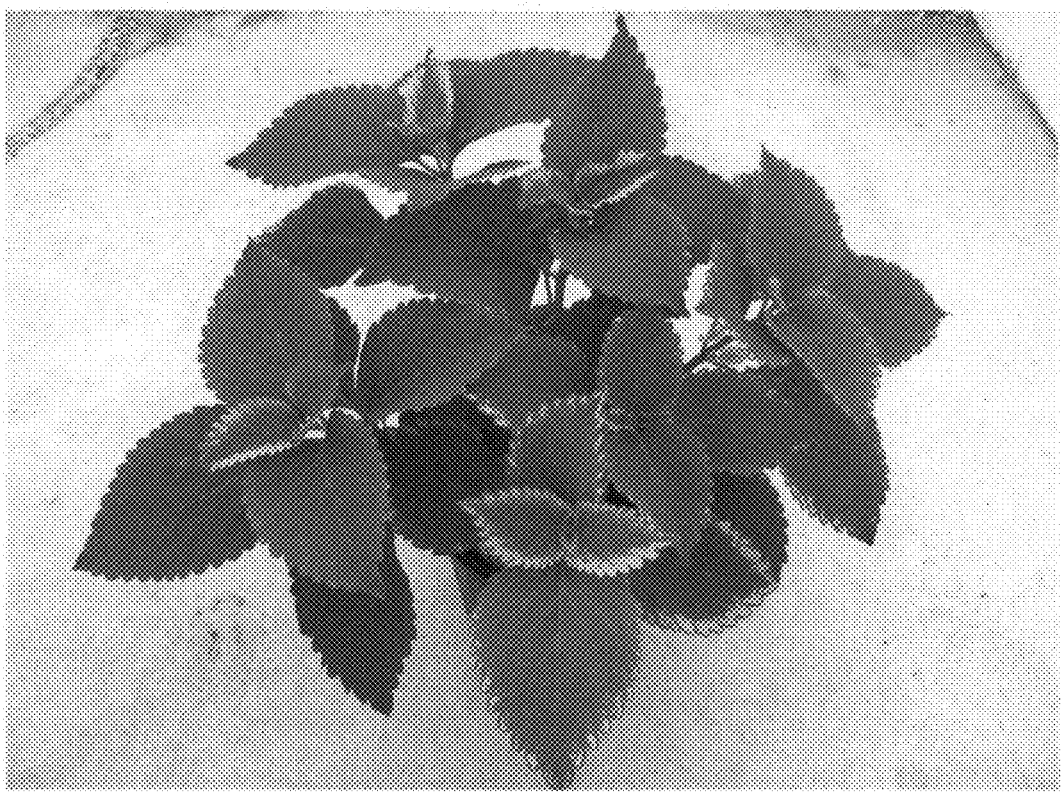
FIGS. 2 and 3 were taken of plants grown for nine weeks from unrooted cuttings that were pinched once at four weeks after stick and grown five additional weeks in November 2014-January, 2015 in a poly-covered plastic greenhouse in Gainesville, Fla.
Figure 3:
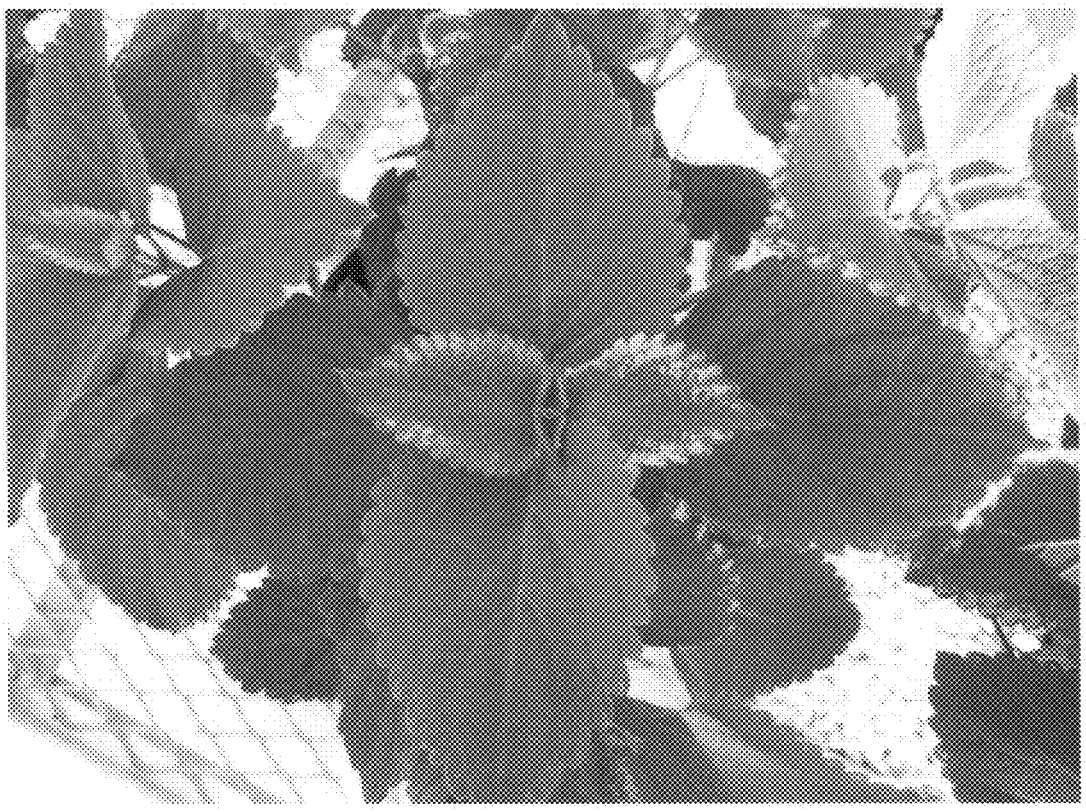

The following detailed description sets forth the distinctive characteristics of 'UF13-42-4'. The detailed description was obtained using eight-week-old plants grown from unrooted cuttings in November 2014-January of 2015 in a poly-covered plastic greenhouse in Gainesville, Fla. The plants were pinched four weeks after cuttings were stuck, then grown in 1-gallon pots for approximately five additional weeks. Color references are to The R.H.S. Colour Chart of The Royal Horticultural Society of London (R.H.S.), 2007 5th Edition.

Classification:

*Family*.—Lamiaceae.

*Botanical*.—*Solenostemon scutellarioides*.

*Common name*.—Coleus.

*Cultivar name*.—'UF13-42-4'.

Plant description:

*Form*.—Spreading.

*Habit*.—Upright.

*Height* (*from top of soil*).—20-25 cm.

*Width* (*horizontal plant diameter*).—40-45 cm.

Propagation:

*Type cuttings*.—Vegetative meristems having at least 1 node.

*Time to initiate roots*.—3-4 days.

*Time to produce a rooted cutting*.—7-10 days.

*Root habit*.—Fibrous.

*Root description*.—Callus forms in 2 to 3 days, roots initiate in 3-4 days and become a highly branched cutting in 7-10 days.

Branches:

*Quantity per plant*.—5-6 main branches per plant with numerous side branches.

*Branch color*.—RHS N187B.

*Texture*.—Smooth.

*Pubescence*.—Not present.

*Stem description*.—Square-shaped stem, 0.5 cm in diameter at the soil line.

*Branch diameter*.—0.4-0.5 cm at the base of an 18-cm long branch.

*Branch length*.—18-20 cm.

*Internode length*.—3.5-4.0 cm.

*Anthocyanin*.—N/A.

Leaves:

*Quantity of leaves per branch*.—12-14.

*Arrangement*.—Opposite.

*Fragrance*.—Not fragrant.

*Shape*.—Ovate.

*Length*.—12-13 cm.

*Width*.—8-9 cm.

*Apex*.—Broadly acuminate.

*Base*.—Attenuate.

*Margin*.—Crenate.

*Leaf texture* (*both surfaces*).—Smooth.

*Pubescence* (*both surfaces*).—Not present.

*Venation color*.—Upper surface: RHS N186D. Lower surface: RHS 145D.

*Venation pattern*.—Upper surface: Arcuate. Lower surface: Arcuate and reticulate.

*Color: Immature leaf*.—Upper surface: Center: RHS 184A; margin: RHS N144A. Lower surface: Center: RHS 187B; margin: RHS N144A.

*Color: Mature leaf*.—Upper surface: Center: RHS 185A; margin: RHS N144C. Lower surface: RHS 187C.

*Petiole length*.—2-3 cm.

*Petiole diameter*.—0.2-0.3 cm.

*Petiole color*.—RHS 183C.

*Petiole texture*.—Smooth.

Flowers and seeds: Flowers and seeds have not been observed to date.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Peronospora lamii*). This pathogen has been observed in stock materials grown closely together in cooler growing seasons.

What is claimed is:

1. A new and distinct *Solenostemon scutellarioides* plant named 'UF13-42-4' as described and illustrated herein.

* * * * *